United States Patent
Aboudheir et al.

(10) Patent No.: US 9,994,512 B2
(45) Date of Patent: Jun. 12, 2018

(54) SYSTEM AND PROCESS FOR RECLAIMING SINGLE AND MIXED AMINE SOLVENTS

(71) Applicant: HTC Purenergy Inc., Regina (CA)

(72) Inventors: Ahmed A. Aboudheir, Regina (CA); Walid H. Elmoudir, Regina (CA)

(73) Assignee: HTC Purenergy Inc., Regina, SK (CA)

( * ) Notice: Subject to any disclaimer, the term of this patent is extended or adjusted under 35 U.S.C. 154(b) by 687 days.

(21) Appl. No.: 14/386,703

(22) PCT Filed: Mar. 28, 2013

(86) PCT No.: PCT/CA2013/050259
§ 371 (c)(1),
(2) Date: Sep. 19, 2014

(87) PCT Pub. No.: WO2013/143001
PCT Pub. Date: Oct. 3, 2013

(65) Prior Publication Data
US 2015/0083576 A1    Mar. 26, 2015

Related U.S. Application Data

(60) Provisional application No. 61/617,309, filed on Mar. 29, 2012.

(51) Int. Cl.
C07C 209/84    (2006.01)
C07C 213/10    (2006.01)
(Continued)

(52) U.S. Cl.
CPC .......... *C07C 209/84* (2013.01); *B01D 1/0064* (2013.01); *B01D 1/0082* (2013.01);
(Continued)

(58) Field of Classification Search
CPC .................. B01D 1/0064; B01D 3/106; B01D 2252/204; B01D 53/1425; B01D 53/1493; B01D 53/96; C07C 209/84
See application file for complete search history.

(56) References Cited

U.S. PATENT DOCUMENTS 2,513,242 A * 6/1950 Inman ..................... F24H 1/101
219/630
2,701,750 A    2/1955 Paulsen et al.
(Continued)

FOREIGN PATENT DOCUMENTS

CA    2673781    7/2008
CA    2789342    8/2011
(Continued)

OTHER PUBLICATIONS

Chinese Office Action, Chinese Application No. 201380018056.3, dated Aug. 11, 2015.
(Continued)

*Primary Examiner* — Bobby Ramdhanie
*Assistant Examiner* — Briana M Obenhuber
(74) *Attorney, Agent, or Firm* — Andrus Intellectual Property Law, LLP (57) ABSTRACT

A processes is for purifying an amine compound from a feed solvent which includes an amine salt of the amine compound. The process includes heating the feed solvent in a single stage evaporator of a reclaimer at a reduced operating pressure by feeding the evaporator with a constant amount of thermal energy; and evaporating the amine compound to purity the amine compound from the feed solvent.

15 Claims, 3 Drawing Sheets

(51) Int. Cl.
  *B01D 53/96* (2006.01)
  *B01D 53/14* (2006.01)
  *B01D 1/06* (2006.01)
  *B01D 1/08* (2006.01)
  *B01D 45/00* (2006.01)
  *B01D 1/00* (2006.01)

(52) U.S. Cl.
  CPC ............ *B01D 1/06* (2013.01); *B01D 53/1425* (2013.01); *B01D 53/1493* (2013.01); *B01D 53/96* (2013.01); *C07C 213/10* (2013.01); *B01D 2252/204* (2013.01); *B01D 2257/302* (2013.01); *B01D 2257/304* (2013.01); *B01D 2257/404* (2013.01); *B01D 2257/504* (2013.01)

(56) References Cited

U.S. PATENT DOCUMENTS

| | | | |
|---|---|---|---|
| 3,664,930 A | | 5/1972 | Pottiez et al. |
| 4,389,383 A | | 6/1983 | Sokolik, Jr. et al. |
| 5,108,551 A | | 4/1992 | Yan |
| 5,137,702 A | | 8/1992 | Yan |
| 5,152,887 A | * | 10/1992 | Beasley .................. B01D 1/02 203/100 |
| 5,389,208 A | | 2/1995 | Beasley et al. |
| 5,441,605 A | | 8/1995 | Beasley et al. |
| 5,993,608 A | | 11/1999 | Abry et al. |
| 6,152,994 A | | 11/2000 | Van Grinsven et al. |
| 6,245,128 B1 | | 6/2001 | George, Jr. |
| 6,508,916 B1 | * | 1/2003 | Razzaghi ........... B01D 53/1425 159/44 |
| 7,323,600 B1 | | 1/2008 | Turoff et al. |
| 8,808,429 B2 | * | 8/2014 | Woodhouse ....... B01D 53/1425 95/183 |
| 2007/0148068 A1 | | 6/2007 | Burgers et al. |
| 2008/0159937 A1 | | 7/2008 | Oulmet |

FOREIGN PATENT DOCUMENTS

| | | | |
|---|---|---|---|
| CN | 1110338 C | 6/2003 | |
| CN | 101657247 | 2/2010 | |
| CN | 201834781 | 5/2011 | |
| EP | 1967250 A1 * | 9/2008 | ......... B01D 53/1425 |
| WO | 9321148 | 10/1993 | |
| WO | 9848920 | 11/1998 | |
| WO | 9921821 | 5/1999 | |
| WO | 0076624 | 12/2000 | |
| WO | 2010/142716 | 12/2010 | |

OTHER PUBLICATIONS

Australian Office Action for Application No. AU2013239292, dated Oct. 12, 2016.
Chinese Office Action with English Translation for Application No. CN2013818056, dated Mar. 29, 2016.
International Preliminary Report on Patentability for Application No. PCT/CA2013/050259, dated Oct. 9, 2014, 6 pages.
Written Opinion for Application No. PCT/CA2013/050259, dated Jul. 2, 2013, 4 pages.
Examination Report issued in corresponding GB Application No. 13768394.2, dated May 17, 2017.
International Search Report for PCT/CA2013/050259 dated May 5, 2013.
Arthur L. Kohl et al., Gas Purification, Fifth Edition, Chapter 3: Mechanical Design and Operation of Alkanolamine Plants, 1 Jan. 1997, Gulf Publishing Company, Houston, TX XP002550025, ISBN: 978-0-88415-220-0.
Supplementary European Search Report, EP Application No. 13768394.2, dated Oct. 15, 2015.
Notification of Third Office Action, Chinese Patent Application No. 201380018056.3, dated Nov. 22, 2016.

* cited by examiner

SYSTEM AND PROCESS FOR RECLAIMING SINGLE AND MIXED AMINE SOLVENTS

CROSS-REFERENCE TO RELATED APPLICATIONS

This application is the U.S. national stage application of International Application PCT/CA2013/050259, filed Mar. 28, 2013, which international application was published on Oct. 3, 2013, as International Publication WO2013/143001 in the English language. The international application is incorporated herein by reference, in entirety. The international application claims priority to U.S. Provisional Patent Application No. 61/617,309, which is incorporated herein by reference.

FIELD

The present disclosure relates generally to a process for thermal reclamation of amine-based solvents.

BACKGROUND

Various processes, such as those used in oil refineries, natural gas processing plants and $CO_2$ capture plants, use an amine-based solvent for acid gas absorption from gaseous streams. For example, amine-based solvent may be used for $CO_2$ capture from flue gas of power plant stations, for $CO_2/H_2S$ absorption from sour natural gas streams or oil refinery tail gas, or for extracting dissolved acid gas species such as $H_2S$ or COS from refinery condensate streams such as liquefied petroleum gas (LPG) or natural gasoline. The acid gas absorption process mainly consists of an absorber to remove acid gases from the gaseous stream, and a stripper to regenerate the amine-based solvent by stripping off the absorbed acid gases from the amine-based solvent.

The amine-based solvent may comprise, for example, a primary-, a secondary-, a tertiary-, and/or a sterically hindered amine compound. Exemplary amines may include monoethanolamine (MEA), diglycolamine (DGA), diethylamine (DEA), di-isopropanolamine (DIPA), triethanolamine (TEA), methyldiethanolamine (MDEA), 2-amino-2-methyl-1-propanol (AMP) or a mixture thereof. In addition to the amine compound, an optional co-solvent, such sulfolane (2,3,4,5-tetrahydrothiophene-1,1-dioxide), poly propylene glycol ether, glycerol, or other organic that is soluble in water, can be present in the amine-based solvent.

Amine-based solvents, for example those single or mixed solvents used to absorb the acid gas, may accumulate or form undesired compounds over time which may affect the ability of the amine-based solvent to absorb the acid gas. Undesired waste compounds may include, for example, high-boiling degradation products, ionic species, impurities, fine suspended solids, or any combination thereof. If the undesired compounds are not removed on an ongoing basis, the amine-based solvent may lose a portion of its absorption capacity and operational challenges may occur, resulting in complications with plant operation effectiveness and plant economics.

Operational challenges in a process that uses amine-based solvents for acid gas absorption may include: increased stripping energy consumption; increased corrosion tendency; changed solvent physical properties; fouling of heat exchangers leading to reduced heat transfer efficiency; formation of foaming in the capture plant columns leading to reduced contact between gas and liquid and reduced acid gas removal; loss of solvent effectiveness; increased operating costs due to greater solvent consumption; or any combination thereof.

A reclaimer unit may be used to treat the amine-based solvent in order to separate the amine compound from accumulated undesired compounds in the amine-based solvent. The types of undesired compounds found in the amine-based solvent are a function of the impurities in the gaseous streams, the type of amine compound used, and the operating conditions of the treating unit in an oil refinery, natural gas processing plant or $CO_2$ capture plant. A reclaimer unit may be used, for example, to remove high-boiling degradation products, ionic species, impurities, fine suspended solids from the amine-based solvent, or any combination thereof.

General processes for reclaiming the amine compound from the amine-based solvent include: thermal reclaiming, ion-exchange, electro-dialysis, mechanical filtration, and adsorption (e.g. using activated carbon). These general processes may be used to separate the amine compound from the degradation products, ionic species, impurities, fine suspended solids present in the amine-based solvent, or any combination thereof. Thermal reclaiming is the only process that can remove the majority of degradation products and contaminants in the amine solvent.

Current thermal reclaimers may be complex, expensive and difficult to operate. They may have reduced recovery rates of the amine compound. The amine compound may comprise a large portion of the reclaimer waste. Existing thermal reclaimers operate at high temperatures which can lead to thermal degradation of the amine compound. If excessive water and steam are used to enhance amine compound recovery, the associated amount of energy used may result in commercially untenable costs. Current thermal reclaimers may have long reclaimer operation cycles, where operation cycles corresponds to the operation time required to meet the cleanup target of the solvent. Current thermal reclaimers may use a cold feed stream (for example, from a storage tank or cold lean-solvent stream) for feeding into the reclaimer, resulting in increased energy consumption and increased heating costs associated with the thermal reclamation process.

Examples of known thermal reclaimer processes are disclosed in: U.S. Pat. No. 2,701,750; U.S. Pat. No. 3,664,930; U.S. Pat. No. 4,389,383; U.S. Pat. No. 5,108,551; U.S. Pat. No. 5,137,702; U.S. Pat. No. 5,152,887; U.S. Pat. No. 5,389,208; U.S. Pat. No. 5,441,605; U.S. Pat. No. 5,993,608; U.S. Pat. No. 6,152,994; U.S. Pat. No. 6,245,128; U.S. Pat. No. 6,508,916; U.S. Pat. No. 7,323,600; International Patent Publication WO 93/21148; International Patent Publication WO 98/48920; International Patent Publication WO 99/21821; International Patent Publication WO 00/76624; and U.S. Patent Publication No. 2007/0148068, the disclosures of which are hereby incorporated by reference.

Existing reclaimers for primary alkanolamine solvents, such as MEA and DGA, may be operated at the operational pressure of the stripper, which could be slightly higher than atmospheric pressure, in order to return the reclaimer product vapour to the stripper from the reclaimer unit. Known reclaimers include kettle reboilers, which have a large vapour space at the top of the kettle reboiler. The heat duty is often supplied by high pressure steam using a horizontal U-tube bundle. For secondary and tertiary amines, such as DEA, DIPA and MDEA, existing reclaimers may be operated under reduced pressure with a single batch evaporator or more than one evaporator in serial.

In operation of existing reclaimers, the concentration of high-boiling organic compounds, nonvolatile salts, or both, will increase as the reclaimer is fed with additional amine-based solvent and the amine compound is removed. At operational pressure of the stripper, this increased concentration of high-boiling organic compounds, nonvolatile salts, or both, may result in a sufficient increase in the temperature of the reclaimer so as to increase the decomposition rate of the amine compound being purified, which could result in loss of amine, formation of volatile decomposition products which could contaminate the purified amine product, or both. High salt concentrations in the reclaimer could result in precipitation of solid crystals which could contribute to reclaimer fouling, plugging problems, or both.

SUMMARY

It is an object of the present disclosure to obviate or mitigate at least one disadvantage of previous thermal reclaimer processes. In contrast to previous thermal reclaimer processes, various embodiments of the reclaiming process of the present disclosure may: consume less energy/steam; provide shorter reclamation cycle; cost less in utility costs; cost less in capital expense; reduce thermal decomposition of the amine; increase solvent recovery; reduce the quantity of waste generated that would require disposal; be easier to operate; be easier to maintain; or any combination thereof.

In one aspect of the disclosure, there is provided a process for purifying an amine compound from a feed solvent. The process includes: heating the feed solvent in a single stage vertical evaporator of a reclaimer at a reduced operating pressure by feeding the evaporator with a constant amount of thermal energy; evaporating the amine compound to purify the amine compound from the feed solvent; replacing the evaporated amine compound with additional feed solvent; varying the operating pressure of the evaporator to maintain the vertical evaporator at a preset temperature and to maintain the evaporation of the amine compound at a preset recovery rate; concentrating reclaiming waste in a waste collector of the vertical evaporator; withdrawing at least a portion of the collected reclaiming waste from the vertical evaporator and replacing the withdrawn reclaiming waste with additional feed solvent. The reclaiming waste is withdrawn from the vertical evaporator when: the content of the amine compound in a vapor output from the single stage evaporator falls below a threshold level; the temperature of the vertical evaporator reaches or exceeds a threshold temperature; the recovery rate of the amine compound falls below a threshold recovery rate; or any combination thereof.

The process may be a continuous process.

The waste collector may hold between 15% and 50% of the total liquid volume in the vertical evaporator. In some examples, the waste collector may hold between 15% and 35% of the total liquid volume in the vertical evaporator. In particular examples, the waste collector may hold between 15% and 25% of the total liquid volume in the vertical evaporator.

The waste collector may be a space in the vertical evaporator with reduced liquid agitation and having a space to collect settled waste. For example, the waste collector may be a space at the bottom of a vertical evaporator vessel and/or vertical sidearm heater. In particular examples, the waste collector is the space in the vertical evaporator vessel below a liquid nozzle that connects a sidearm heater to the vertical evaporator vessel, where the height below the liquid nozzle is between 10% and 50% of the total liquid height in the vertical evaporator vessel. In some examples, the height below the liquid nozzle is between 10% and 35% of the total liquid height in the vertical evaporator vessel. In particular examples, the height below the liquid nozzle is between 10% and 25% of the total liquid height in the vertical evaporator vessel.

The feed solvent may include a plurality of amine compounds, amine salts, or both and the process may additionally include: further reducing the pressure to a second reduced operating pressure; heating the feed solvent by feeding the vertical evaporator with the constant amount of thermal energy; and purifying an additional amine compound from the feed solvent.

Water, steam, or both may be added to the feed solvent. The steam may be saturated, low pressure steam, and may be sparged into the vertical evaporator.

The process may further include withdrawing the reclaiming waste from the reclaimer under vacuum. Reclaiming waste may include a high boiling degradation compound, heat stable salt, solid, or any combination thereof.

The feed solvent may include an amine salt of the amine compound and the process may include neutralizing with a base at least a portion of the amine salt to liberate the amine compound. The base may be added in a basic solution which is: at least a 50 wt % solution of sodium hydroxide or potassium hydroxide in water, at least a 40 wt % solution of sodium hydroxide or potassium hydroxide in water, at least a 30 wt % solution of sodium hydroxide or potassium hydroxide in water, or at least a 20 wt % solution of sodium hydroxide or potassium hydroxide in water.

The reduced operating pressure may be between 100 and 3 kPa.

The feed solvent may be heated using low pressure steam at a constant rate and conditions. The low pressure steam may be obtained from an oil refinery, natural gas processing plant, $CO_2$ capture plant utilities, waste energy recovery boilers, or steam produced as by-product from a chemical process.

Withdrawing the reclaiming waste from the vertical evaporator may include withdrawing the reclaiming waste from the vertical evaporator while adding additional feed solvent, water, steam or any combination thereof to the reclaimer to compensate for the removed waste.

In another aspect of the disclosure, there is provided a reclaiming system for purifying an amine compound from a feed solvent. The system includes: a single stage vertical solvent evaporator unit for separating the amine compound from the added solvent by evaporation, the vertical evaporator unit including an inlet for the feed solvent; an evaporator vessel in fluid communication with the inlet; a heater for providing thermal energy to the evaporator unit at a constant rate; a waste collector for collecting reclaiming waste; and a liquid outlet in fluid communication with the waste collector to remove collected reclaiming waste from the reclaiming system. The system also includes: a vacuum pump for reducing the operating pressure of the reclaiming system; a condenser unit in fluid communication with the vertical evaporator unit and for accepting the separated amine compound from the solvent evaporator unit; and a liquid/gas separator unit in fluid communication with the condenser unit to separate the condensed amine compound from non-condensable gases, providing a purified amine compound.

The single stage vertical evaporator unit may further include an inlet for sparging steam into the feed solvent in the single stage vertical solvent evaporator unit.

The single stage vertical evaporator unit may further include an inlet for adding water into the feed solvent in the single stage vertical solvent evaporator unit.

The evaporator vessel may be a vertical evaporator vessel having the waste collector located therein.

The heater may be a vertical sidearm heater having the waste collector located therein.

The feed solvent may include an amine salt of the amine compound and the system may also include a mixer for mixing a base with the feed solvent. The base may be added in a basic solution which is: at least a 50 wt % solution of sodium hydroxide or potassium hydroxide in water, at least a 40 wt % solution of sodium hydroxide or potassium hydroxide in water, at least a 30 wt % solution of sodium hydroxide or potassium hydroxide in water, or at least a 20 wt % solution of sodium hydroxide or potassium hydroxide in water.

A particular example of a system according to the present disclosure includes: a single stage vertical solvent evaporator unit for separating the amine compound from the added solvent by evaporation, the vertical evaporator unit having: an inlet for the feed solvent; a vertical evaporator vessel in fluid communication with the inlet and comprising a first waste collector for collecting reclaiming waste; a vertical sidearm heater providing thermal energy to the evaporator vessel at a constant rate, the vertical sidearm heater in fluid communication with the evaporator vessel and comprising a second waste collector for collecting reclaiming waste; and at least one liquid outlet in fluid communication with the first and/or second waste collectors to remove the collected reclaiming waste from the reclaiming system. The exemplary system also includes: a vacuum pump for reducing the operating pressure of the reclaiming system; a condenser unit in fluid communication with the vertical evaporator unit and for accepting the separated amine compound from the solvent evaporator unit; and a liquid/gas separator unit in fluid communication with the condenser unit to separate the condensed amine compound from non-condensable gases, providing a purified amine compound.

A waste collector according to the present disclosure may hold between 15% and 50% of the total liquid volume in the vertical evaporator. In some examples, the waste collector may hold between 15% and 35% of the total liquid volume in the vertical evaporator. In particular examples, the waste collector may hold between 15% and 25% of the total liquid volume in the vertical evaporator.

The waste collector may be a space in the vertical evaporator with reduced liquid agitation and having a space to collect settled waste. For example, the waste collector may be a space at the bottom of a vertical evaporator vessel and/or vertical sidearm heater. In particular examples, the waste collector is the space in the vertical evaporator vessel below a liquid nozzle that connects a sidearm heater to the vertical evaporator vessel, where the height below the liquid nozzle is between 10% and 50% of the total liquid height in the vertical evaporator vessel. In some examples, the height below the liquid nozzle is between 10% and 35% of the total liquid height in the vertical evaporator vessel. In particular examples, the height below the liquid nozzle is between 10% and 25% of the total liquid height in the vertical evaporator vessel.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Generally, the present disclosure provides a process for reclaiming an amine compound from a feed solvent. The reclaiming process includes: purifying the amine compound using a single stage vertical evaporator; varying the operating pressure of the vertical evaporator to maintain the vertical evaporator at a preset temperature and to maintain the evaporation of the amine compound at a preset recovery rate; concentrating reclaiming waste in a waste collector of the vertical evaporator; withdrawing at least a portion of the reclaiming waste from the vertical evaporator; and replacing the evaporated amine compound and the withdrawn reclaiming waste with additional feed solvent.

The reclaiming waste is withdrawn from the vertical evaporator when the content of the amine compound in a vapor output from the single stage evaporator falls below a threshold level; the temperature of the vertical evaporator reaches or exceeds a threshold temperature; the recovery rate of the amine compound falls below a threshold recovery rate; or any combination thereof. Reclaiming waste may include a high boiling degradation compound, heat stable salt, solid, or any combination thereof.

A "single stage evaporation process" shall be understood to refer to an evaporation process that is conducted in one evaporator vessel or a plurality of evaporator vessels in a parallel configuration, where the evaporator vessels are all substantially at the same operating temperature and pressure. "Substantially at the same temperature" shall be understood to mean that the difference between the temperature of any two vessels is no more than 10% of the average of the temperatures of the two vessels. Similarly, "substantially at the same pressure" shall be understood to mean that the different between the pressure of any two vessels is no more than 10% of the average of the pressures of the two vessels.

This is differentiated from a multi-stage evaporation process, which is conducted by evaporation using at least two connected evaporator vessels in a serial configuration, where each evaporator vessel is operated at a different temperature, pressure, or both.

The single stage, reduced pressure evaporation process maintains the evaporator at a preset temperature by varying the operating pressure while the evaporator is fed a constant amount of thermal energy. A "preset temperature" shall be understood to mean that the temperature does not vary more than 10% from a desired operating temperature, where the desired operating temperature is the temperature required to recover the targeted amines based on their boiling points. In some examples, it is desirable for the preset temperature to vary less than 5% from the desired operating temperature. In other examples, it is desirable for the preset temperature to vary less than 2% from the desired operating temperature.

Varying the operating pressure of the single stage, reduced pressure evaporation process allows the recovery rate to be maintained at a preset recovery rate. A "preset recovery rate" shall be understood to mean that the recovery rate of the amine compound does not vary more than 10% from a desired recovery rate.

Varying the operating pressure may be desirable, for example, when purifying from the feed solvent a mixture of amine compounds, each having a different boiling point. By reducing the operating pressure, each amine compound could be separately evaporated at their reduced boiling point temperatures. Purifying an amine compound using a single stage, reduced pressure evaporation process maintained at a preset temperature may be advantageous in plants such as oil refineries, natural gas processing plants and $CO_2$ capture plants since operators may not be required to change to a higher temperature source (for example a higher temperature steam) during the process in order to achieve an elevated temperature. Furthermore, maintaining a preset temperature avoids degradation of the amine compound that would otherwise occur if the operating temperature was raised above the thermal decomposition temperature.

A vertical evaporator (or vertical evaporator unit) includes at least one vertical evaporator vessel and/or at least one vertical sidearm heater that provides a waste collector for collecting reclaiming waste, such as a high boiling degradation compound, heat stable salt, solid, or any combination thereof, at the bottom of the vertical evaporator vessel and/or vertical sidearm heater, thereby facilitating removal of the reclaiming waste. A vertical evaporator may concentrate the reclaiming waste in the waste collector of the vertical evaporator vessel and/or vertical sidearm heater to a greater extent than traditional evaporator used in traditional reclaimers. A more concentrated waste reduces associated waste volume for disposal and its subsequent costs.

The waste collector in the vertical evaporator vessel and/or vertical sidearm heater has reduced amounts of agitation, or no agitation, for example agitation by liquid flow, in comparison to the liquid movement at a liquid nozzle that connects a sidearm heater to the evaporator vessel.

The waste collector may hold between 15% and 50% of the total liquid volume in the vertical evaporator. In some examples, the waste collector may hold between 15% and 35% of the total liquid volume in the vertical evaporator. In particular examples, the waste collector may hold between 15% and 25% of the total liquid volume in the vertical evaporator.

The waste collector may be a space in the vertical evaporator with reduced liquid agitation and having a space to collect settled waste. For example, the waste collector may be a space at the bottom of a vertical evaporator vessel and/or vertical sidearm heater. In particular examples, the waste collector is the space in the vertical evaporator vessel below a liquid nozzle that connects a sidearm heater to the vertical evaporator vessel, where the height below the liquid nozzle is between 10% and 50% of the total liquid height in the vertical evaporator vessel. In some examples, the height below the liquid nozzle is between 10% and 35% of the total liquid height in the vertical evaporator vessel. In particular examples, the height below the liquid nozzle is between 10% and 25% of the total liquid height in the vertical evaporator vessel.

A vertical evaporator shall be understood to mean an evaporator having a vertical evaporator vessel and/or vertical sidearm heater which is taller than it is wide. In particular examples, the height (H) to diameter (D) ratio is at least about 3.5:1.

The sizing of the vertical evaporator vessel may be based on the specified residence time of the liquid being fed to the vertical evaporator unit. The vertical evaporator vessel may be designed to be half full of liquid in order to provide sufficient vertical disengaging space for the separation of entrained liquids. Within the top, vapor section of the vertical evaporator vessel, the diameter may be larger to provide sufficient volume space to accommodate the liquid feed flashing at the feed nozzle inlet.

In a particular embodiment, the process includes reclaiming a mixture of amine compounds from a feed solvent. The reclaiming process includes: purifying the mixture of amine compound using a vertical, single stage reduced pressure evaporation process. The single stage reduced pressure evaporation process maintains the evaporator at a preset temperature by varying the operating pressure in order to separately evaporate each amine compound at their respective boiling point temperatures. The feed solvent may include a mixture of amine salts and the process may include adding a base to neutralize at least a portion of the mixture of amine salts and regenerate the mixture of amine compounds.

A reduced pressure reclaiming process according to the present disclosure may be used for distillation of temperature sensitive materials. Organic compounds may decompose at certain temperatures (i.e. decomposition temperatures), so a vacuum may be applied in order to reduce the operating pressure and thereby reduce the operating temperature of the reclaiming process. This reduced temperature reduces solvent degradation, which may otherwise occur at the higher temperature.

Adding liquid water, steam, or both to the feed solvent reduces the temperature required for reclaiming the amine compound, and thereby possibly increases the recovery rate, since the added water, steam, or both, reduces the amine partial pressure. By applying a vacuum to the evaporator, and optionally adding water, steam, or both, the boiling points of the amine compounds are depressed, thereby allowing the amine compound to be evaporated at a lower temperature than in a system working at elevated pressure.

The vertical evaporator is heated to its operating temperature using a heater. The heat source for the heater may be, for example: low pressure steam, direct gas firing, or waste heat generated by the processing plant which is operating the reclaimer. The low pressure steam may be low pressure saturated steam. Low pressure steam is understood to mean steam at about 600 kPa or less. The low pressure steam may be used to directly or indirectly heat the solvent in the evaporator. Directly heating the solvent in the evaporator would be understood to include heating the solvent using a heat exchanger located inside a vertical evaporator vessel. Indirectly heating the solvent in the evaporator would be understood to include removing the solvent from the evaporator vessel, heating the removed solvent, and returning the solvent to the evaporator vessel. The liquid solvent may be moved from the evaporator vessel to the heater using a liquid transfer nozzle and the heated vapor may be moved back to the evaporator vessel using a vapor transfer nozzle. One specific example of indirectly heating the solvent is a vertical sidearm heater. The vertical sidearm heater provides a waste collector for reclamation waste at the bottom of the vertical sidearm heater, thereby facilitating removal of the waste. The waste may be removed under vacuum while the reclaiming process is in operation, for example when it is in continuous operation.

Systems according to the present disclosure include: a vertical evaporator vessel, a vertical sidearm heater, or both. As noted above, a vertical evaporator vessel and a vertical sidearm heater provide a waste collector for collecting reclaiming waste at the bottom of the vessel or heater, respectively, thereby facilitating removal of the reclaiming waste.

Figure 1:
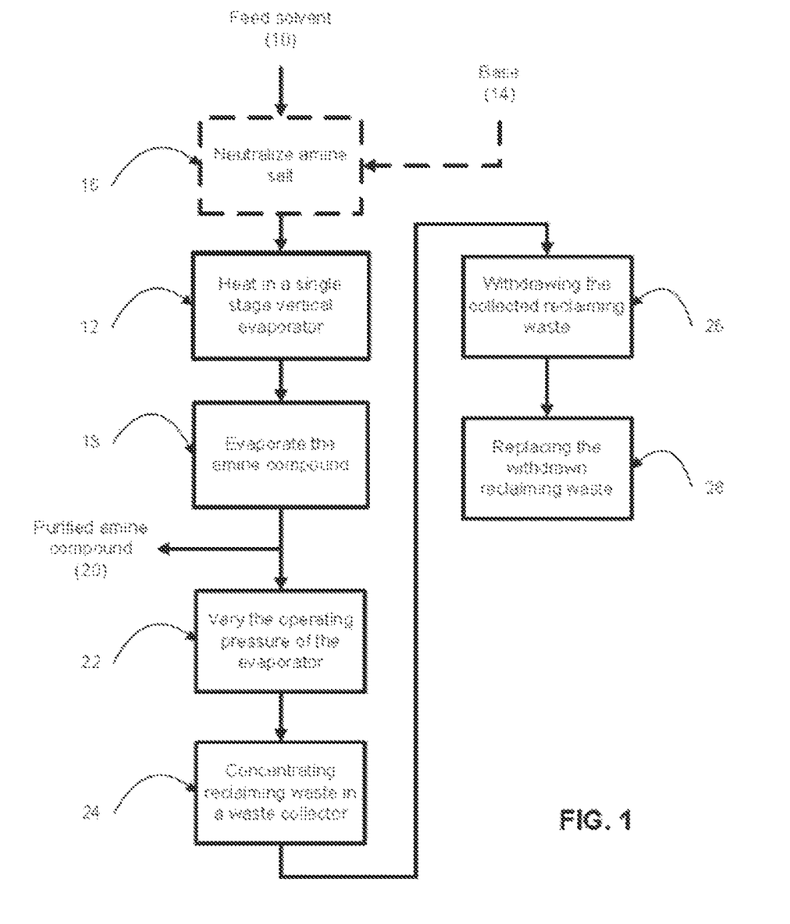
FIG. 1 illustrates a reclaiming process according to the present disclosure.

An exemplary reclaiming process according to the present disclosure is illustrated in FIG. 1. In the exemplary process, a feed solvent (10) that includes an amine compound is heated in a single stage vertical evaporator at (12). If the feed solvent (10) includes an amine salt, then a base (14) may be added at (16) to neutralize the amine salt. The feed solvent, or the mixture containing the neutralized amine salt, is added to a reclaimer and heated in a single stage vertical evaporator to evaporate the amine compound at (18) and produce the purified amine compound (20). The vertical evaporator is fed a constant amount of thermal energy. The amine salt may be, for example, produced in an oil refinery, a natural gas processing plant, or a $CO_2$ capture plant from the reaction of an amine compound with an acid gas such as $CO_2$, $H_2S$, $SO_x$, $NO_x$, or with another impurity in the gas feed, such as oxygen. Reaction of the base with the amine salt liberates the corresponding amine compound from the amine salt for reclamation.

In addition to the amine compound and amine salt, the feed solvent (10) may include one or more co-solvents, one or more additional amine compounds, one or more additional amine salts, or any combination thereof. The co-solvents, additional amine compounds, additional amine salts, or any combination thereof, may be purified by evaporation, may be withdrawn from the reclaimer as waste, or may be partially purified by evaporation and partially withdrawn from the reclaimer as waste.

A vacuum may be applied to the reclaimer to reduce the boiling point of the amine compound of the feed solvent (10). It would be understood that the vacuum could be applied to the reclaimer before the feed solvent (10) was added in order to bring the reclaimer to the reduced operating pressure. Depending on the physical properties of the amine compound to be reclaimed, the reclaiming process may be operated at a reduced pressure relative to standard atmospheric pressure, for example in the range from 100 to 3 kPa.

Reducing the operating pressure of the evaporator reduces the operating temperature and, therefore, reduces the rate of formation of thermal degradation products, which is beneficial when reclaiming compounds whose degradation temperatures are close to the boiling points of the compound at a higher pressure. Examples of such compounds may include, for example, secondary amines, tertiary amines, organic co-solvents such as sulfolane, or any combination thereof.

The operating pressure of the vertical evaporator is varied at (22) during evaporation to maintain the evaporator at a preset temperature and to maintain the evaporation of the amine compound at a preset recovery rate.

Reclaiming waste is concentrated in a waste collector of the vertical evaporator at (24). The concentrated waste collected in the vertical evaporator, for example the vertical evaporator vessel and/or vertical sidearm heater, is withdrawn at (26), for example using a positive displacement pump, when: the content of the amine compound in the vapor output falls below the threshold level; the temperature of the evaporator reaches or exceeds a threshold temperature; the recovery rate of the amine compound falls below a threshold recovery rate; or any combination thereof. Withdrawn reclaiming waste is replaced with additional feed solvent at (28). Using a positive displacement pump allows the reclaimer to be kept under vacuum when in operation. It would be understood that withdrawal of waste could be achieved using alternative methods, for example by allowing the reclaimer to return to atmospheric pressure and draining the waste by gravity.

In the exemplary reclaiming process, the feed solvent (10) is added to the reclaimer as the purified amine compound (20) is removed from the reclaimer, and reclamation of the purified amine compound (20) results in an increased concentration of reclamation waste in a waste collector of the vertical evaporator. Reclamation waste may include: a high boiling degradation compound, heat stable salt, solid, or any combination thereof. The increased concentration of high-boiling compounds, nonvolatile salts, or both, results in an increase in the temperature of the evaporator until the temperature reaches a threshold temperature, at which point the reclaiming process may continue with the addition of water, steam, or both, but where the addition of feed solvent to the reclaimer is reduced or stopped. The reclamation process may be continued in this manner (i.e. with the addition of water, steam, or both, to the reclaimer but with little or no feed solvent (10) being added to the reclaimer) until the content of the amine compound in a vapor output drops below a threshold level (for example less than 2 wt %). The threshold may be specified, for example, based on the constituents of the solvent and their degradation temperatures.

The feed solvent may include a mixture of different amine compounds, amine salts, or both. In a mixture of different amine compounds, the process may separate one amine compound from other amine compounds, or may separate a mixture of amine compounds from a different mixture of amine compounds.

The solvent (10) is evaporated at (18) to provide the purified amine compound (20). The feed solvent (10) added to the reclaimer may be provided from the bottom of a stripper at the stripper temperature, which may reduce the heat duty required by the reclaimer to evaporate the mixture.

During the reclaiming process, water, steam, or both may be added and mixed in the reclaimer. For example, the steam may be low pressure steam sparged into the reclaimer, for example into the feed solvent in an evaporator. The low pressure steam may be saturated steam. Adding water, steam, or both reduces the amine partial pressure and increases recovery rate.

The base (14) used to liberate the amine compound from the amine salt is chosen depending on the amine compound being reclaimed and the type and concentration of the amine salt. In general terms, reaction of an acid (HA) and an amine ($NR_3$) results in an amine salt ($R_3NH^+A^-$). Addition of a base ($B^-$) to the amine salt ($R_3NH^+A^-$) results in the following equilibrium reaction:

A base that is stronger than the amine shifts the equilibrium to the right of the reaction, while a base that is weaker than the amine shifts the equilibrium to the left of the reaction. NaOH, KOH, $Na_2CO_3$, $K_2CO_3$ or mixtures thereof are examples of bases that may be used for liberation of the amine compound from the amine salt.

Figure 2:
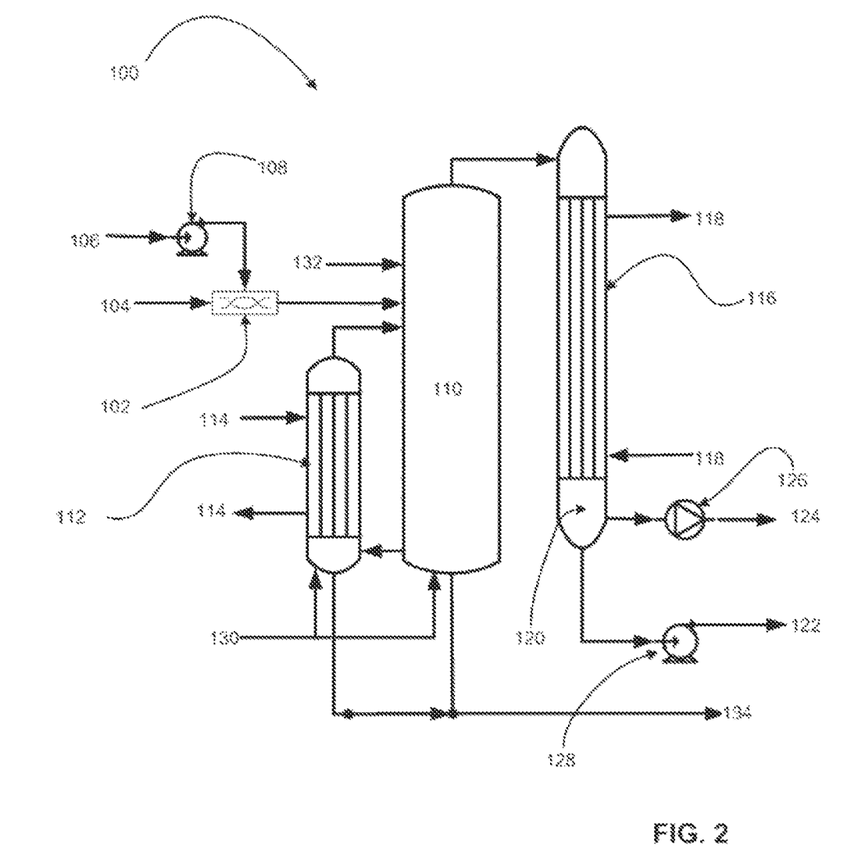
FIG. 2 illustrates a reclaiming system which may be used to practice a reclaiming process according to the present disclosure.

An exemplary reclaiming system, which may be used to practice the process according to the present disclosure, is illustrated in FIG. 2. The exemplary reclaimer (100) includes: an in-line mixer unit (102) for mixing a feed solvent (104) which includes an amine salt, and a basic solution (106); a chemical injection pump (108); a single stage vertical evaporator vessel (110) in fluid communication with a vertical sidearm heater (112) having an inlet and outlet for low pressure steam (114), the low pressure steam for providing thermal energy to the feed solvent in the single stage vertical evaporator vessel; a condenser unit (116) with an inlet and outlet for coolant (118); a liquid/gas separator (120) to separate purified amine compound (122) from non-condensable gases (124); a vacuum pump unit (126) for reducing the pressure of the reclaimer (100) to the reduced operating pressure; and a solvent condensate pump (128) to remove the recovered amine from the system continuously under vacuum. In addition to the amine compound and corresponding amine salt, the feed solvent (104) may further include a one or more co-solvents, one or more additional amine compounds, one or more additional amine salts, or any combination thereof.

As illustrated in the exemplary system of FIG. 2, steam (130), water (132), or both, may be added to the system during the reclamation process. The steam may be low pressure steam, for example low pressure steam generated by the processing plant which is operating the reclaimer system (100). The steam may be sparged into the vertical evaporator vessel (110) and/or the vertical sidearm heater (112). Water may be added to the vertical evaporator vessel (110). In addition to reducing the partial pressure of the amine compound, steam, water or both, may be used to control the level of liquid (i.e. "level control") in the vertical evaporator vessel (110) or vertical sidearm heater (112). Waste may be removed from the system via waste stream (134) to enhance the solvent recovery rate. As illustrated in the exemplary system of FIG. 2, waste is removed from the waste collector of the vertical evaporator vessel, the vertical sidearm heater, or both. The waste may be removed from the waste collector by a positive displacement pump (not shown) while the reclaimer is under vacuum, such as during operation. The waste may be removed while the reclaimer is in continuous operation.

The feed solvent (104) may be a slipstream from a total lean solvent stream. For example, the slipstream may be 0.5 to 2% of the total lean stream in circulation within the acid gas purification plant. The feed solvent may be withdrawn from the bottom of a stripper of the acid gas purification plant by gravity, by the reduced pressure within the reclaimer, or by both. The feed solvent (104) may be fed to the reclaimer system (100) at the stripper operating temperature, thereby reducing the heat duty of the reclaiming process.

The basic solution (106), which comprises a base, for example sodium hydroxide or potassium hydroxide, is added to liberate the amine compound from corresponding heat-stable amine salt. In particular embodiments, at least 50 wt % sodium hydroxide or potassium hydroxide in water is used. In other embodiments, at least 40 wt % sodium hydroxide or potassium hydroxide in water is used. In further embodiments, at least 30 wt % or less sodium hydroxide or potassium hydroxide in water is used. However, it would be understood that the total amount of basic solution added would increase as the concentration of the base decreased in order to provide sufficient molar amounts of base to liberate the amine compound from the amine salt.

If low pressure steam (130), for example saturated steam, is sparged into the evaporator unit, the sparged steam quality may be similar to the quality of the steam (114) that is fed to the vertical sidearm heater (112), for example the steam may be at about 360 kPa pressure. Feed solvent (104) may be fed to the vertical evaporator vessel (110) on level control; and water (132), steam (130), or both, may be injected to control the temperature within the evaporator vessel (110).

It is preferable that the liquid level of the feed solvent in the vertical evaporator vessel (110) be maintained at a level where tubes/plates in the sidearm heater (112) are filled with the liquid during the reclaimer operation since low pressure steam (114) may be supplied to the shell side/hot plates of the sidearm heater (112) when the tubes are filled with liquid. It would be understood that the liquid filling the evaporator vessel (110) comprises the feed solvent, any basic solution, water, any degradation products, any impurities, or any combination thereof.

Multiple operating cycles may be carried out by changing only the operating pressure, for example within the range from 100 to 3 kPa. Changing the operating pressure may be achieved by adjusting the vacuum target of the vacuum pump (126) while maintaining constant flow of low pressure steam (114) to the vertical sidearm heater (112) and adding the feed solvent (104) to the vertical evaporator vessel (110) on level control.

In exemplary processes, the different pressures of the multiple operating cycles may be determined based on the chemical composition of the feed solvent. For example, in a feed composition having a mixture of three different amine compounds, a first operating pressure may be determined based on the desired operating temperature that corresponds to the lowest boiling point of the three amine compounds. The second operating pressure may be determined based on the desired operating temperature that corresponds to the next lowest boiling point of the three amine compounds. The third operating pressure may be determined based on the desired operating temperature that corresponds to the highest boiling point of the three amine compounds. The three operating cycles would then be carried out by changing the operating pressure from the first operating pressure, to the second operating pressure, and finally to the third operating pressure, while the evaporator is fed with a constant amount of thermal energy, such as the saturated steam (114) shown in FIG. 2.

In other exemplary processes, the different pressure of the multiple operating cycles may be established based on a stepwise reduction between a first operating pressure and a final operating pressure. For example, the process may be first carried out at an operating pressure of, for example, 50 kPa. After a period of time, the operating pressure may be reduced to, for example, 40 kPa, while the evaporator is fed with a constant amount of thermal energy, such as the saturated steam (114) shown in FIG. 2. After another period of time, the operating pressure may be reduced to, for example, 30 kPa, while the evaporator is fed with a constant amount of thermal energy, such as the saturated steam (114) shown in FIG. 2. Additional stepwise reductions in operating pressure may be undertaken until a final operating pressure of, for example, 10 kPa is achieved. Each step between each operating pressure may be the same or different from other steps.

The purified amine compound (122) and the associated water vapor, which have been condensed in the condenser unit (116), may be returned to the refinery, natural gas processing plant or $CO_2$ capture plant. Any non-condensable gases (124) obtained from the reclaimer may be removed by a vacuum pump (126) and may be, for example, combusted in a flare (for example in the case of a natural gas processing plant) or discharged to a safe location (for example with the off-gas in a CO₂ capture plant).

Figure 3:
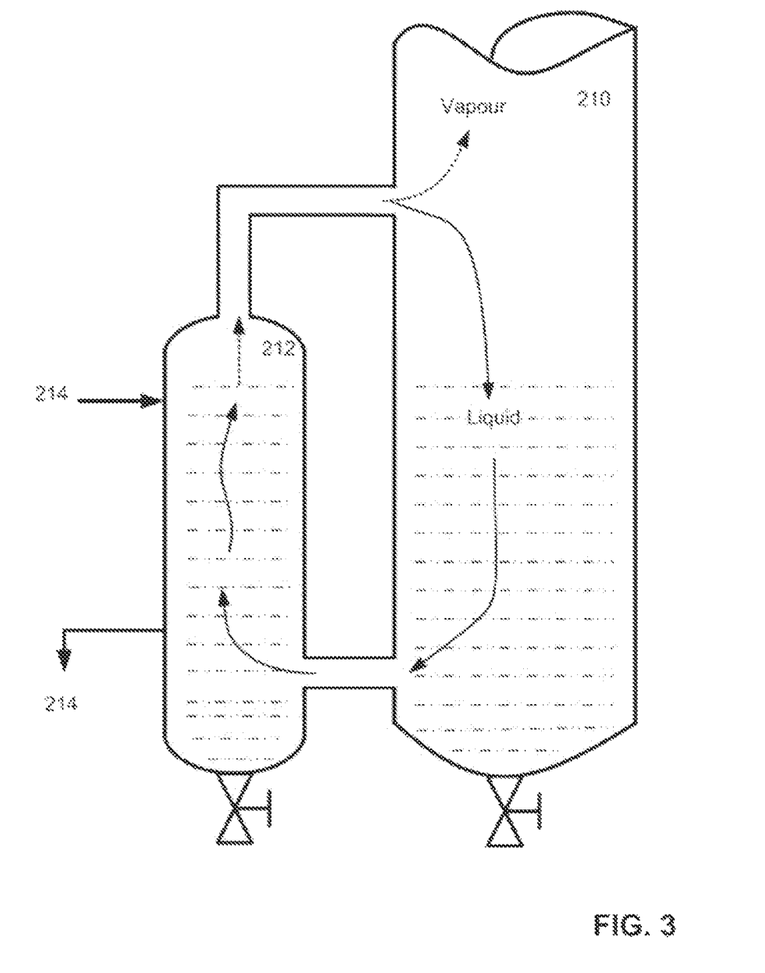
FIG. 3 illustrates an evaporator unit and sidearm heater which may be used in the reclamation system illustrated in FIG. 2.

One example of a vertical evaporation vessel and vertical sidearm-heater arrangement which may be used in a reclamation system according to the present disclosure is illustrated in FIG. 3. The vertical design/orientation of the evaporation vessel (210) and sidearm-heater (212) facilitates continued heating of solvent using a natural circulation, thermosiphon configuration where liquid flows from the vertical evaporator vessel (210) to the vertical sidearm-heater (212) via a liquid transfer nozzle, and where vapor flows from the vertical sidearm-heater (212) to the vertical evaporator vessel (210) via a vapour transfer nozzle. In such a configuration, liquid in the vertical sidearm-heater (212) is transformed into a vapour by heating using low pressure steam (214), which circulates into the vertical evaporation vessel (210). Components of the vapour which condense into liquid are recirculated to the vertical sidearm-heater (212), while components of the vapour which remain gaseous are transferred to the condenser unit (not shown).

In addition, the vertical vessel orientation of the evaporation chamber and sidearm heater provides waste collector for reclamation waste, such as a high boiling degradation compound, heat stable salt, solid, or any combination thereof, at the waste collector of the evaporator, the sidearm heater, or both, which facilitates collection and removal of the waste from the bottom of the vertical evaporator and/or vertical sidearm heater.

The waste collector of the example illustrated in FIG. 3 is free of agitation by liquid flow because it is the spaces located below the liquid transfer nozzle at the bottom of the evaporator vessel and at the bottom of the sidearm-heater. As described above, the waste collector may hold between 15% and 50% of the total liquid volume in the vertical evaporator. The height below the liquid nozzle may be between 10% and 50% of the total liquid height in the vertical evaporator vessel.

The exemplary vertical side-arm heater (212) may be used in a reclamation system that uses a non-vertical evaporation vessel. The vertical design/orientation of the sidearm-heater (212) facilitates continued heating of solvent using a natural circulation, thermosiphon configuration. In such a configuration, liquid in the vertical sidearm-heater (212) is transformed into a vapour by heating using low pressure steam, which circulates into a non-vertical evaporation vessel. The vertical vessel orientation of the sidearm heater provides waste collector for reclamation waste, such as sludge and degradation products, at the bottom of the sidearm heater, which facilitates concentration and removal of the waste from the bottom of the sidearm heater.

In the preceding description, for purposes of explanation, numerous details are set forth in order to provide a thorough understanding of the examples. However, it will be apparent to one skilled in the art that these specific details are not required.

The above-described examples are intended to be exemplary only. Alterations, modifications and variations can be effected to the particular examples by those of skill in the art without departing from the scope, which is defined solely by the claims appended hereto.

The invention claimed is:

1. A reclaiming system for purifying an amine compound from a feed solvent, the system comprising:
    a single stage vertical solvent evaporator unit for separating the amine compound from the feed solvent by evaporation, the vertical evaporator unit comprising:
        an inlet for the feed solvent;
        a vertical evaporator vessel in fluid communication with the inlet and comprising a first waste collector for collecting reclaiming waste from the vertical evaporator vessel;
        a vertical sidearm heater providing thermal energy to the solvent evaporator unit at a constant rate, the vertical sidearm heater in fluid communication with the evaporator vessel and configured to receive liquid from the vertical evaporator vessel and to provide vapor comprising a separated amine compound and non-condensable gases to the vertical evaporator vessel, and comprising a second waste collector for collecting unevaporated reclaiming waste from the vertical sidearm heater; and
        at least one liquid outlet in fluid communication with the first and second waste collectors to remove the collected reclaiming waste from the reclaiming system;
    a vacuum pump reducing the operating pressure of the reclaiming system;
    a condenser unit in fluid communication with the vertical evaporator unit and accepting the separated amine compound vapor from the solvent evaporator unit to form a condensed amine compound; and
    a liquid/gas separator unit in fluid communication with the condenser unit to separate the condensed amine compound from the non-condensable gases, providing a purified amine compound.

2. The reclaiming system according to claim 1, wherein the single stage vertical solvent evaporator unit further comprises an inlet for sparging steam into the feed solvent in the single stage vertical solvent evaporator unit.

3. The reclaiming system according to claim 1, wherein the single stage vertical solvent evaporator unit further comprises an inlet for adding water into the feed solvent in the single stage vertical solvent evaporator unit.

4. The reclaiming system according to claim 1, wherein the reclaiming system further comprises a mixer configured to mix a base with the feed solvent.

5. A process for purifying an amine compound from a feed solvent that includes heat stable salts and suspended solid impurities, the process comprising:
    heating the feed solvent in a single stage vertical evaporator of the reclaiming system of claim 1 under vacuum by feeding the single stage vertical evaporator with a constant amount of thermal energy;
    evaporating the amine compound to purify the amine compound from the feed solvent;
    replacing the evaporated amine compound with additional feed solvent;
    operating the single stage vertical evaporator under vacuum to maintain the temperature of the amine compound at its boiling point temperature;
    collecting reclaiming waste in a waste collector of the single stage vertical evaporator;
    withdrawing at least a portion of the collected reclaiming waste from the single stage vertical evaporator while the single stage vertical evaporator is under vacuum when:
        a) a content of the amine compound in a vapor output from the single stage vertical evaporator falls below a threshold level;
        b) the temperature of the single stage vertical evaporator reaches or exceeds a threshold temperature;
        c) a recovery rate for the amine compound falls below a threshold recovery rate for the amine compound; or d) any combination thereof, and replacing the withdrawn reclaiming waste with additional feed solvent.

6. The process according to claim 5, wherein water, steam, or both is added to the feed solvent.

7. The process according to claim 5, wherein low pressure saturated steam is sparged into the feed solvent in the single stage vertical evaporator.

8. The process according to claim 5, wherein the feed solvent includes an amine salt of the amine compound, and the process further includes neutralizing, with a base, at least a portion of the amine salt to liberate the amine compound.

9. The process according to claim 8, wherein the base is added in a basic solution which is: at least a 50 wt % solution of sodium hydroxide or potassium hydroxide in water.

10. The process according to claim 8, wherein the base is added in a basic solution which is: at least a 40 wt % solution of sodium hydroxide or potassium hydroxide in water.

11. The process according to claim 8, wherein the base is added in a basic solution which is: at least a 30 wt % solution of sodium hydroxide or potassium hydroxide in water.

12. The process according to claim 8, wherein the base is added in a basic solution which is: at least a 20 wt % solution of sodium hydroxide or potassium hydroxide in water.

13. The process according to claim 5, wherein the vacuum pressure is between 100 kPa and 3 kPa.

14. The process according to claim 5, wherein heating the feed solvent is done using low pressure steam at a constant rate and at constant conditions.

15. The process according to claim 14, wherein the low pressure steam is obtained from an oil refinery, natural gas processing plant, $CO_2$ capture plant, utilities, waste energy recovery boilers, or steam produced as by-product from a chemical process.

* * * * *